United States Patent [19]

Dahl et al.

[11] Patent Number: 5,200,530
[45] Date of Patent: Apr. 6, 1993

[54] KETO REDUCTION OF CARBACYCLIN INTERMEDIATES

[75] Inventors: Helmut Dahl; Gabriela Buttner; Dieter Peschel, all of Berlin, Fed. Rep. of Germany

[73] Assignee: Schering Aktiengesellschaft, Berlin and Bergkamen, Fed. Rep. of Germany

[21] Appl. No.: 772,762

[22] Filed: Jul. 31, 1991

Related U.S. Application Data

[63] Continuation of Ser. No. 237,112, Jul. 13, 1988, filed as PCT/DE87/00519, Nov. 12, 1987, abandoned.

[30] Foreign Application Priority Data

Nov. 13, 1986 [DE] Fed. Rep. of Germany ......... 368761

[51] Int. Cl.$^5$ .............................................. C07F 7/04
[52] U.S. Cl. ................................. 549/214; 549/336; 549/332; 556/441; 560/119; 562/501
[58] Field of Search ...................... 549/214, 336, 332; 556/441; 560/119; 562/501

[56] References Cited

FOREIGN PATENT DOCUMENTS 136779 4/1985 European Pat. Off. .

Primary Examiner—Nicky Chan
Attorney, Agent, or Firm—Millen, White, Zelano and Branigan

[57] ABSTRACT

The invention relates to a new process for the reduction of 15-keto carbacyclin intermediates in the presence of cerium(III) Salts.

9 Claims, No Drawings

KETO REDUCTION OF CARBACYCLIN INTERMEDIATES

This is a continuation of application Ser. No. 07/237,112 filed Jul. 13, 1988, filed as PCT/DE87/00519, filed Nov. 12, 1987, now abandoned.

The invention relates to a new process for the reduction of 15-keto carbacyclin intermediates (PG nomenclature) in the presence of cerium(III) salts.

In the syntheses of pharmacologically effective carbacyclin analogs Iloprost, Cicaprost or Eptaloprost, reduction of the 15 keto group to the 15alpha hydroxy group is a very important step. Reduction with technically easily available reagents such as sodium borohydride leads to a mixture with undesirable 15beta hydroxy isomers. The two isomers must be separated from one another by chromatography. (For economical reasons the 15beta isomer must be reoxidized to the initial ketone and again reduced and separated into the 15 isomers, etc.) The expense necessary for the separation (adsorbent, amount of solvent) is higher, the more 15beta hydroxy isomer must be separated.

According to present processes the portion of undesirable 15beta hydroxy isomers is always high, if reduction with simple hydride reagents is involved.

Moreover, Iloprost, which represents a diastereomer mixture of 16-methyl compounds in a ratio of 16alpha:1-6beta=54:46, so far is obtained in this way only if said reoxidation is performed once or twice and all 15alpha hydroxy products (which by themselves exhibit different diastereomeric compositions), obtained after reduction and chromatography, are further processed together. The chemical reaction, as can easily be seen, requires exceptionally high expenses.

In Iloprost synthesis the 15-keto group (3a, diagram 1) can also be reduced microbiologically (to 4a). But the total expense of performing a microbiological reduction, working up and purification of the product up to separation of the undesirable accompanying substances is very high.

Microbiological reduction cannot be performed in the case of Cicaprost and Eptaloprost intermediate step 1.

It cannot be performed in the case of 3b either. 3b can be produced by simultaneously filed syntheses by 3alpha-hydroxy-cis-bicyclo[3.3.0]octan-7-one-2beta-carboxylic acid methyl ester derivatives, especially 7,7-neopentyl ketal, in a substantially simpler way than present precursor 3a.

Diagram 1

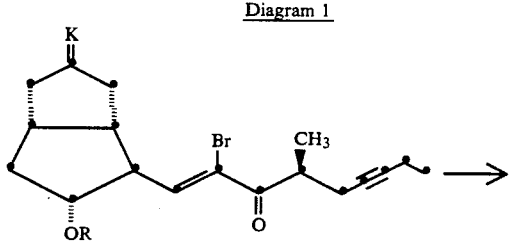

1 a: K = —O—CH$_2$—CH$_2$—O—
R = —CO—C$_6$H$_5$
b: K = —O—CH$_2$—C(CH$_3$)$_2$—CH$_2$—O—

R = —CO—⟨C$_6$H$_4$⟩—C$_6$H$_5$ c: K = —O—CH$_2$—C(CH$_3$)$_2$—CH$_2$—O—
R = —Si(CH$_3$)$_2$[C(CH$_3$)$_3$]

-continued
Diagram 1

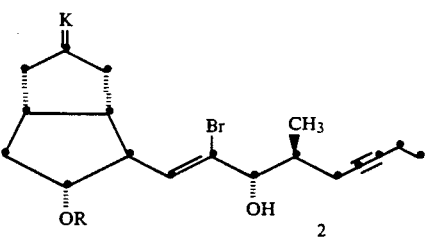

2

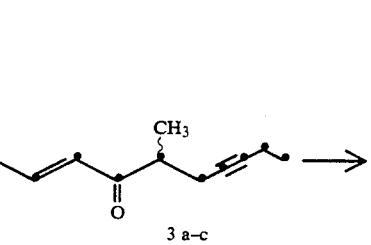

3 a–c

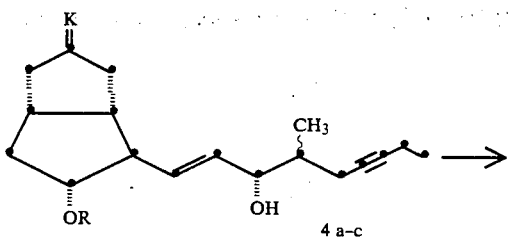

4 a–c

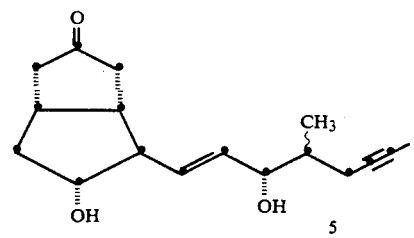

5 a) K = —O—CH$_2$—CH$_2$—O—
   R = —CO—C$_6$H$_5$
b) K = —O—CH$_2$—C(CH$_3$)$_2$—CH$_2$—O
   R = —Si(CH$_3$)$_2$C(CH$_3$)$_3$
c) K = —O—CH$_2$—C(CH$_3$)$_2$—CH$_2$—O—

R = —O—⟨THP⟩ d) K = —O—CH$_2$—C(CH$_3$)$_2$—CH$_2$—O—
   R = Si(CH$_3$)$_2$[C(CH$_3$)$_2$CH(CH$_3$)$_2$]
e) K = —O—CH$_2$—C(CH$_3$)$_2$—CH$_2$—O—
   R = Si(C$_6$H$_5$)$_2$[C(CH$_3$)$_3$]

The ketone 3c obtainable from the THP ether precursors (instead of said silyl ethers) leads, in the case of sodium borohydride reduction, to poorer yields and to an unsatisfactory 16-diastereomer distribution. Moreover, the 15-isomers can be separated only after cleavage of the protecting groups, which makes the usability of the 15beta portion by reoxidation difficult. The route by 3c therefore is less favorable than by 3b.

The object therefore was to improve the chemical reduction of the 15-keto group in the synthesis of carbacyclin analogs relative to the yield of 15alpha-hydroxy product and also in Ilosprost synthesis relative to the 16-diastereomer composition.

Thus, the invention relates to a process for the production of alpha-hydroxy-bicyclo[3.3.0]octane derivatives of formula I

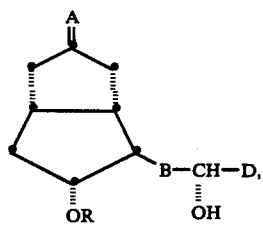

in which

A means the double bond radical —O—X—O— with X as straight-chain or branched-chain alkylene with 1–7 C atoms or the radicals =CH—(CH$_2$)$_3$—COOR′, =CH—CH$_2$—O—CH$_2$—COOR′ or =CH—(CH$_2$)$_3$—O—CH$_2$—CH$_2$-COOR′ with R′ as C$_1$–C$_7$ alkyl, R means

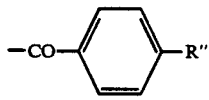

with R″ as hydrogen or phenyl or the radical —SiR$_1$R$_2$R$_3$, and R$_1$, R$_2$ and R$_3$ can be the same or different and represent a straight-chain or branched-chain alkyl group with 1–7 C atoms or phenyl, B means a trans-CH=C(X) group with X as hydrogen or bromine, and the trans-configuration relates to the C chain, and D means an alkyl group with 1–10 C atoms, an alkenyl group with 2–10 C atoms or an alkynyl group with 2–10 C atoms, characterized in that, keto-bicyclo[3.3.0]octane derivatives of formula II (II)

is the presence of cerium(III) salts.

In attaining this object, two effects are important, which, individually, but especially combined with one another, are advantageous.

a) Performance of the reduction with sodium borohydride in the presence of cerium(III) chloride leads to a marked yield increase in the desired 15alpha-hydroxy product.

| Reaction | Reduction agent | 15α-OH:15β-OH | Yield Increase | Example |
|---|---|---|---|---|
| 1a→2a | NaBH$_4$ | 40:60 | } 35% | 1b |
|  | NaBH$_4$/CeCl$_3$ | 54:46 |  | 1a |
| 1b→2b | NaBH$_4$ | 46:54 | } 22% | 2b |
|  | NaBH$_4$/CeCl$_3$ | 56:44 |  | 2a |
| 1c→2c | NaBH$_4$/CeCl$_3$ | 89:11 |  | 4 |

The yield increase thus amounts to more than 100%, if the protecting group effect is also considered.

Production of 1c takes place analogously to the production of 1a from the carbaldehyde described in example A 1.

For using the obtained compound 2c the same processes are suitable, which are suitable for using compounds 2a and 2b. Cleavage of the protecting groups takes place analogously to example A 3.

b) Influence of protecting groups

This includes the replacement of 11-esters used so far with 11-silyl ethers.

| Reaction | Reduction agent | 15α-OH:15β-OH | 16α-CH$_3$:16β-CH$_3$ | Yield Increase | Example |
|---|---|---|---|---|---|
| 3a→4a | NaBH$_4$ | 55:45 | 60:40 |  |  |
|  | NaBH$_4$/CeCl$_3$ | 55:45 | 60:40 |  |  |
| 3b→4b | NaBH$_4$/CeCl$_3$ | 89:11 | 54:46 | } 60% | 3a |
|  | NaBH$_4$ | 74:26 | 59:41 |  | 3b |
| 3c→4c | NaBH$_4$/CeCl$_3$ | 67:33 | 57:43 |  |  |

The high yield with the reduction according to the invention of 3b to 4b has the result that the 16-methyl diastereomer distribution is also correct, by which the reoxidation of the 15beta-OH portion can be eliminated, chromatography is made easier and a readily available initial material for synthesis of Iloprost can be used.

(+)-3alpha-hydroxy-7,7-(2,2-dimethyl-trimethylenedioxy)-cisbicyclo[3.3.0]octane-2beta-carboxylic acid methyl ester, produced, e.g., according to German application P 36 38 758.4, is converted into silyl ether according to the process indicated by H. Wetter and K. Oertle, Tetrahedron Letters 26, 5515 (1985) or S. Hanessian and P. Lavallee, Can. J. Chem. 53, 2975 (1975) and the carboxylic acid methyl ester group is reduced analogously to the conditions described by K. Mori and M. Tsuji, Tetrahedron 42, 435 (1986), but to −40° C. The further reaction takes place as described in examples A 1 and A 2. Thexyl dimethyl chlorosilane and tert-butyl-diphenyl chlorosilane are used as silyl chlorides.

Cleavage of the protecting groups from resulting compound 4d takes place analogously to example A 3. In compound 4e cleavage of the protecting groups generally takes place successively. The silyl ether, is cleaved e.g., with tetrabutyl ammonium fluoride in tetrahydrofuran and the ketal is cleaved under the conditions of example A 3. These steps can be interchanged. In all cases compound 5 results.

The addition of cerium(III) chloride in the reduction of 15-keto prostaglandin intermediates is known (J.-L. Luche, J. Amer. Chem. Soc. 100, 2226 (1978), J. C. S. Chem. Comm. 1978, 601). However, it serves to avoid undesirable 1,4-additions, i.e., the reduction of the C$_{13}$–C$_{14}$ double bond. Nothing is known so far about an improvement of the 15alpha/beta ratio in the products. On the contrary, with the use of this method of operation no change but rather a worsening of the yield of 15alpha-hydroxy products is noted, as is represented in the following table of two examples.

Diagram 2

| Feedstock | Reduction agent | 15α/15β-OH |
|---|---|---|
| (structure) | NaBH$_4$ | 50:50 |
|  | NaBH$_4$/CeCl$_3$ | 45:55 |
| (structure) | NaBH$_4$ | 50:50 |
|  | NaBH$_4$/CeCl$_3$ | 50:50 |

Therefore, it is surprising that cerium(III) chloride markedly increases the 15alpha-hydroxy portion in the reduction of the compounds of formula II.

Initial materials are preferred which can be produced from easily available carbacyclin precursors with the use of commercial and sufficiently stable protecting groups. However, the use of the reaction according to the invention is not to be limited by this choice.

Use of sodium borohydride and cerium(III) chloride is preferred, because they are easily obtainable in a large amount. But the reduction could also be performed with other borohydrides and other cerium(III) salts, if they do not decompose under the reaction conditions.

Sodium borohydride must be used in at least stoichiometric amounts. Cerium(III) salts, on the other hand, can even be limited to catalytic amounts Cerium(III), which can be used both in anhydrous form and as hydrate or solution, is preferred.

Suitable solvents have a sufficient solubility for the reactants and do not react with them in the selected temperature range. Methanol is preferred; further there can be used by themselves or in mixture: ethanol, tetrahydrofuran, dimethylformamide and others, optionally with addition of water.

Low temperatures (−100° to 0° C.) promote the formation of 15alpha-hydroxy isomers. Depending on the choice of the reaction conditions, the reaction times are between a few minutes and a few hours.

Production of 1a and 3a as well as the reaction of compounds 2a, 4a and 5 to carbacyclin analogs is known (1a, 2a: European Patent Application 119 949; 3a, 4a, 5: European Patent Specification 11 591).

Analogously to the known processes (diagram 2), 3b is produced from (1S,2S,3R,5R)-3-tert-butyldimethyl-silyloxy-7,7,-(2,2-dimethyltrimethylenedioxy-2-hydroxy-methyl-bicyclo[3.3.0]octane (6) (examples A1 and A2). The protecting groups can be removed in reduction product 4b by acid treatment with formation of the already known 5.

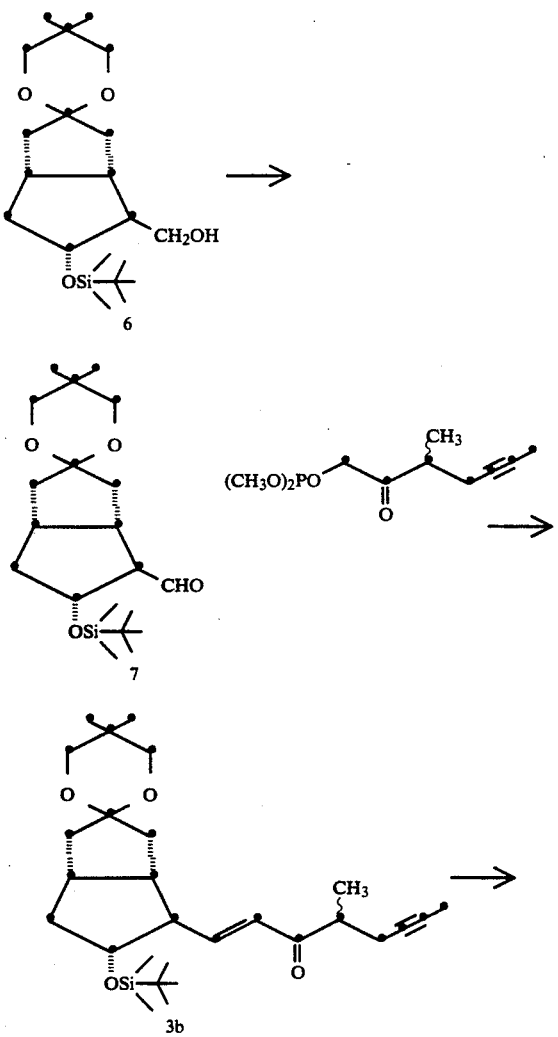

-continued
Diagram 2

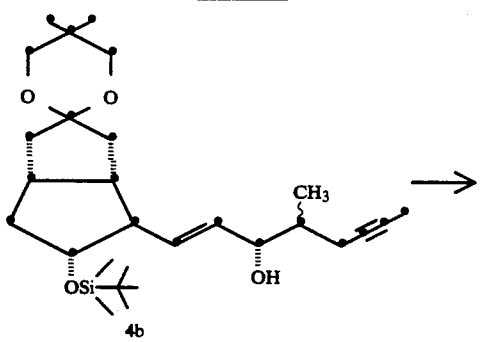
4b

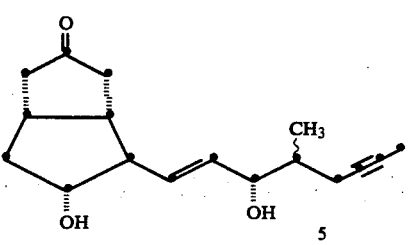
5

The process can also be extended to series, represented by formulas 8 and 9, with the naturally configured subchain (example 7).

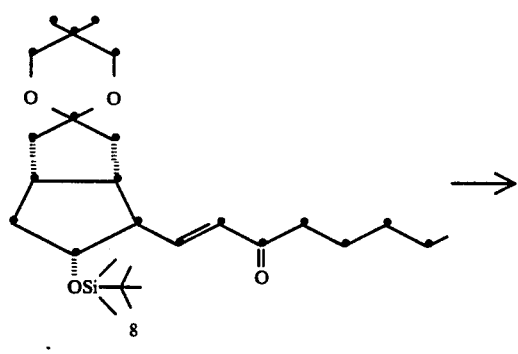
8

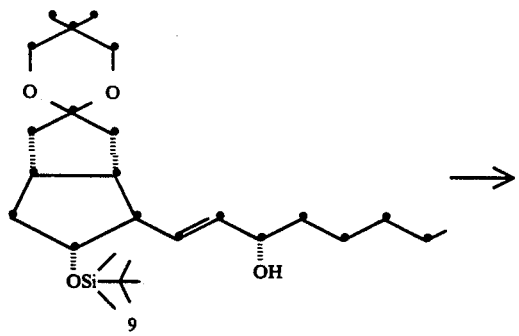
9

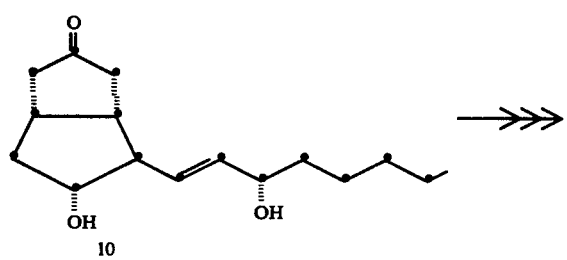
10

-continued

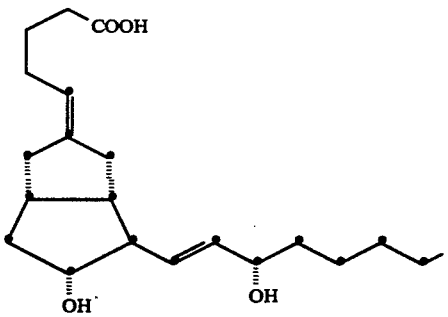
11

Production of initial material 8 takes place according to example A 4.

Use of reduction product 9 for synthesis of unsubstituted carbacyclin 11 takes place by cleavage of the protecting groups according to example A 5 to compound 10. Production of carbacyclin from 10 was already described by Kojima et al., Chem. Phar. Bull. 33, 2588 (1985).

If X means a straight-chain or branched-chain alkylene radical with 1-7 C atoms, the following radicals are meant by it: —$CH_2)_2$ with n=1-7 (methylene, ethylene, tri-, tetra-, penta-, hexa- and hepta-methylene, —$C(CH_3)_2$—, —$CH(CH_3)$—, —$CH(CH_3)$—$CH_2$—, —$C(CH_3)_2$—$CH_2$—, —$CH_2$—$CH(CH_3)$—, $CH_2$—$C(CH_3)_2$—, —$CH_2$—$CH(CH_3)$—$CH_2$—, —$CH_2$—$C(CH_3)_2$—$CH_2$—, —$CH(C_2H_5)$—, —$C(C_2H_5)_2$, —$CH(C_2H_5)$—$CH_2$—, —$C(C_2H_5)_2$—, —$CH_2$—$CH(C_2H_5)$, —$CH_2$—$C(C_2H_5)_2$—, —$CH_2$—$CH(C_2H_5)$—$CH_2$—, —$CH_2$—$C(C_2H_5)_2$- etc.

By R, $R_1$, $R_2$ and $R_3$ as $C_1$-$C_7$ alkyl are understood methyl, ethyl, n-propyl, isopropyl, n-butyl, isobutyl, sec-butyl, tertbutyl, n-pentyl, isopentyl, sec-pentyl, neopentyl, n-hexyl, isohexyl, heptyl, etc.

D as alkyl groups with 1-10 C atoms means, besides the above-named alkyl radicals, also octyl, nonyl, decyl and the respective branched isomers.

D as alkenyl group with 2-10 C atoms preferably means

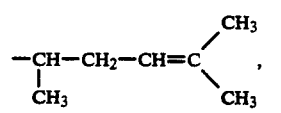

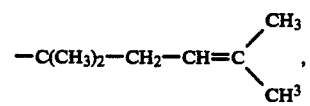

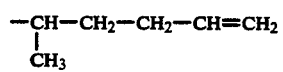

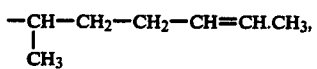

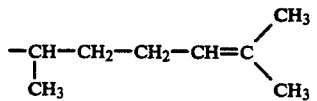

D as alkynyl group with 2-10 C atoms means, for example

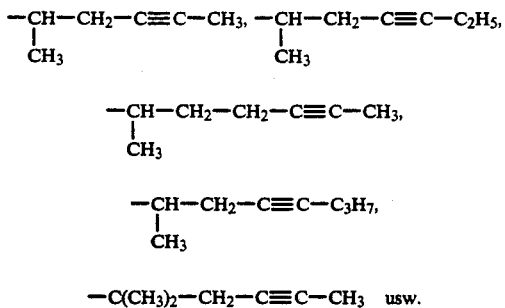

—C(CH₃)₂—CH₂—C≡C—CH₃ usw.

The following embodiments should explain the invention in greater detail.

EXAMPLE A 1

(1S,2R,3R,5R)-7,7-(2,2-dimethyl-trimethylenedioxy)-3-tertbutyldimethylsilyloxy-bicyclo[3.3.0]octane-2-carbaldehyde 1.38 g of oxalyl chloride is dissolved in 20 ml of dichloromethane, cooled to −60° C. and mixed with 1.87 g of dimethyl sulfoxide in 6 ml of dichloromethane. After 10 minutes a solution of 2.886 g of (−)-(1S,2S,3R,5R)-7,7-(2,2-dimethyltrimethylenedioxy)-3-tert-butyldimethylsilyloxy-2-hydroxy-methylbicyclo[3.3.0] octane in 13 ml of dichloromethane is added and stirred for 30 minutes. Then 2.42 g of triethylamine is instilled into 5 ml of dichloromethane. After 2 hours, it is allowed to warm to 0° C., 260 ml of ice water is added, the organic phase is separated, it is washed with sodium chloride solution, dilute citric acid solution and again with sodium chloride solution. After drying with sodium sulfate and removal of the solvent in a vacuum, about 3.0 g of the title compound is obtained as raw product, which can be used without further purification.

EXAMPLE A 2

(1S,2S,3R,5R)-7,7-(2,2-dimethyl-trimethylenedioxy)-3-tertbutyldimethylsilyloxy-2-[(4R,S)(1E)-4-methyl-3-oxo-oct-1-en-6-inyl]bicyclo[3.3.0]octane 0.447 g of sodium hydride (55%) is suspended in 39 ml of tetrahydrofuran, cooled in an ice bath and mixed with 2.58 g of racemic 3-methyl-2-oxo-hept-5-in-yl phosphonic acid dimethyl ester in 20 ml of tetrahydrofuran. It is stirred for 20 minutes and the 3.0 g of the carbaldehyde, obtained in example A 1, is added in 39 ml of tetrahydrofuran. After 3 hours at ice bath temperature and 45 minutes at room temperature it is neutralized with acetic acid, concentrated in a vacuum, taken up in dichloromethane, washed with sodium bicarbonate and sodium chloride solution, dried with sodium sulfate, the solvent is removed and the residue is chromatographed on silica gel with hexane-ethyl acetate mixtures. 3.68 g of the product with [alpha]$_D$+1.0°, [alpha]$_{365}$+26.6° (CHCl₃, c=1) is obtained, which is suitable for further reaction.

EXAMPLE A 3

(1S,2S,3R,5R)-3-hydroxy-2-[(3S,4RS)(E)-3-hydroxy-4-methyl-oct-1-en-6-inyl]-bicyclo[3.3.0]octan-7-one 2.278 g of the nonpolar product obtained according to example 3a is dissolved in 9 ml of tetrahydrofuran, 32.5 ml of acetic acid and 17.5 ml of water and heated for 4 hours to 45° C. Then it is distilled off in a vacuum, finally with addition of toluene, it is taken up in dichloromethane, extracted with water, dried with sodium sulfate, concentrated in a vacuum and chromatographed on silica gel with hexane-ethyl acetate mixtures. 1.26 g of the title compound is obtained which is chromatographically and spectroscopically identical with the material according to the synthesis method described earlier, which exhibits the composition of the 16-diastereomers necessary for the production of Iloprost and whose enantiomer purity (determined by HPLC of the MTPA esters) is greater than 99%.

EXAMPLE A 4

(1S,2S,3R,5R)-7,7-(2,2-dimethyl-trimethylenedioxy)-3-tertbutyldimethylsilyloxy-2-[(1E)-3-oxo-oct-1-enyl]-bicyclo[3.3.0]octane 113 mg of sodium hydroxide (55%) is suspended in 10 ml of tetrahydrofuran and mixed at 20° C. with 630 mg of 2-oxo-heptylphosphonic acid dimethyl ester in 4.5 ml of tetrahydrofuran. It is stirred for 30 minutes and then 1.0 g of the carbaldehyde obtained as in example A 1 is added in 9 ml of tetrahydrofuran. After 5 hours it is neutralized with acetic acid, concentrated in a vacuum, taken up in dichloromethane, washed with sodium chloride solution, dried with sodium sulfate, the solvent is removed and the residue is chromatographed on silica gel with hexane/tert- butyl methyl ether mixtures. 1.19 g of product with [alpha]$_D$+2.3° (chloroform, c=1) is obtained.

EXAMPLE A 5

(1S,2S,3R,5R)-3-hydroxy-2-[(3S)(E)-3-hydroxy-oct-1-enyl]-bicyclo[3.3.0]octan-7-one 0.54 g of the nonpolar product obtained according to example 7 is dissolved in 9 ml of ethanol, mixed with 6 ml of water and 0.06 ml of conc. hydrochloric acid and stirred for 3 hours at room temperature. Then it is neutralized with sodium bicarbonate, distilled off in a vacuum, taken up in ethyl acetate, extracted with sodium chloride solution, dried with sodium sulfate, concentrated in a vacuum and chromatographed on silica gel with hexane/ethyl acetate mixtures. 0.27 g of the title compound is obtained with [alpha]$_D$−11.2° (methanol, c=1). Kojima et al. (1.c.) indicate −11.5° (methanol, c=1).

EXAMPLE 1

(1S,2S,3R,5R)-2-[(1Z)(3S,4S)-2-bromo-3-hydroxy-4-methyl-non-1-en-6-inyl]-7,7-ethylenedioxy-3-benzoyloxy-bicyclo[3.3.0]octane a) According to the invention 107.53 g (1S,2S,3R,5R)-2-[(1Z)(4S)-2-bromo-4-methyl-3-oxonon-1-en-6-inyl]-7,7-ethylenedioxy-3-benzoyloxybicyclo[3.3.0]octane is dissolved in 2 liters of methanol, cooled to −40° C., mixed with 11.68 g of cerium(III) chloride heptahydrate, stirred for 15 minutes, then 12.37 g of sodium borohydride is introduced in portions, stirred 30 minutes, acetone in excess is instilled, stirred another 30 minutes, neutralized with acetic acid, warmed and distilled off in a vacuum. The residue is dissolved in dichloromethane and water, washed with water, dried with sodium sulfate, concentrated in a vacuum and chromatographed on silica gel with dichloromethane/ethyl acetate mixtures.

55.2 g of the title compound is obtained as nonpolar isomer besides 47.0 g of polar 3'R isomer (15alpha:15beta=54:46).

b) Comparison batch

The reaction described under a) is performed but without cerium(III) chloride. To achieve complete reaction, the amount of sodium borohydride must be increased. The isomers are obtained in a ratio of 40:60.

EXAMPLE 2

(1S,2S,3R,5R)-2-[(Z)(3S,4S)-2-bromo-3-hydroxy-4-methyl-non-1-en-6-inyl]-7,7-(2,2-dimethyl-trimethylenedioxy)-3-(4-phenylbenzoyloxy)-bicyclo[3.3.0]octane a) According to the invention 56.5 g of (1S,2S,3R,5R)-2-[(Z)(3S,4S)-2-bromo-4-methyl-3-oxo-non-1-en-6-inyl)-7,7-(2,2-dimethyl-trimethylenedioxy)-3-(4-phenyl-benzoyloxy)-bicyclo[3.3.0]octane is reacted, according to the conditions of example 1, with 5.28 g of sodium borohydride in the presence of 4.96 g of cerium(III) chloride heptahydrate, and 30.06 g of nonpolar 3'S compound, besides 23.62 g of polar 3'R compound, (15alpha:15beta=56:44) is obtained.

b) Comparison batch

The reaction described under a) is performed but without cerium(III) chloride and with an increased amount of sodium borohydride. Isomers in a ratio of 15alpha:15beta=46:54 are obtained.

EXAMPLE 3

(1S,2S,3R,5R)-7,7-(2,2-dimethyl-trimethylenedioxy)-3-tertbutyldimethylsilyloxy-2-[(3S,4RS)(1E)-4-methyl-3-hydroxy-oct-1-en-6-inyl]bicyclo[3.3.0]octane a) According to the invention 3.50 g of the ketone of example A 2 is dissolved in 100 ml of methanol and cooled to −75° C. 2.76 g of cerium(III) chloride heptahydrate is added, stirred for 1 hour, mixed with 0.51 g of sodium borohydride and stirred another 45 minutes at −75° C. After addition of acetone, it is slowly warmed, neutralized with acetic acid and concentrated in a vacuum. The residue is dissolved in dichloromethane, extracted with water, dried with sodium sulfate and concentrated in a vacuum. It is chromatographed on silica gel with hexane/tert-butylmethylether mixtures and 2.52 g of the title compound [non polar isomer, $[alpha]_D+8.8°$, $[alpha]_{365}+24.2°$ (CHCl$_3$), c=1)] and 0.25 g of the polar 3'R isomer are obtained.

HPLC measurements show that in the title compound the methyl isomers are present in a ratio of alpha:beta=54:46.

b) Comparison batch

The reaction described under a) is performed but without cerium(III) chloride and with an increased amount of sodium borohydride. Isomers in a ratio of 3'S:3'R=74:26 are obtained.

Methyl isomers are present in the 3'S portion in a ratio of alpha:beta=59:41.

EXAMPLE 4

(1S,2S,3R,5R)-2-[(1Z)(3S,4S)-2-bromo-3-hydroxy-4-methyl-non-1-en-6-inyl]-7,7-(2,2-dimethyl-trimethylenedioxy)-3-(4-tertbutyl-dimethylsilyloxy-bicyclo[3.3.0]octane 106.0 g of (1S,2S,3R,5R)-2-[(1Z) (3S)-2-bromo-4-methyl-3-oxo-non-1-en-6-inyl]-7,7-(2,2-dimethyl-trimethylenedioxy)-3-(4-tert-butyldimethylsilyloxy-bicyclo[3.3.0]octane is reduced according to example 3. The 15alpha/15beta isomers according to HPLC are present in the raw product in a ratio of 88.9:11.1. In the separation of the mixture by chromatography, 92.2 g of the nonpolar 15alpha-hydroxy isomer $[alpha]_D+21°$ (chloroform, c=1) and 8.0 g of polar 15beta-hydroxy isomer are obtained.

EXAMPLE 5

(1S,2S,3R,5R)-7,7-(2,2-dimethyl-trimethylenedioxy)-3-(2,3-dimethyl-but-2-yl)-dimethyl-silyloxy-2-[(3S,4RS) (1E)-4-methyl-3-hydroxy-oct-1-en-6-inyl]bicyclo[3.3.0]octane 4.5 g of (1S,2S,3R,5R)-7,7-(2,2-dimethyl-trimethylenedioxy)-3-(2,3-dimethyl-but-2-yl)-dimethyl-silyloxy-2[(4RS) (1E)-4-methyl-3-oxo-oct-1-en-6-inyl]-bicyclo[3.3.0]octane is reduced according to example 3a). 3.16 g of nonpolar 15alpha-hydroxy isomer $[alpha]_D+3.0°$ (chloroform, c=1), 0.65 g of polar 15beta-hydroxy isomer and 0.57 g of mixed fractions are obtained.

HLPC measurements after cleavage of the protecting groups shows that the methyl isomers are present in a ratio of alpha:beta=54:46.

EXAMPLE 6

(1S,2S,3R,5R)-7,7-(2,2-dimethyl-trimethylenedioxy)-3-tertbutyldiphenylsilyloxy-2-[(3S,4RS) (1E)-(4-methyl-3-hydroxy-oct-1-en-6-inyl]bicyclo[3.3.0]octane 3.0 g of (1S,2S,3R,5R)-7,7-(2,2-dimethyl-trimethylenedioxy)-3-tert-butyldiphenylsilyloxy-2-[(4RS) (1E)-4-methyl-3-oxo-oct-1-en-6-inyl]bicyclo[3.3.0]octane is reduced according to example 3a. 2.60 g of the nonpolar 15alpha-hydroxy isomer $[alpha]_D 21.1°$ (chloroform, c=1) and 0.35 g of the polar 15beta-hydroxy isomer, which still contains some 15alpha-hydroxy isomer, are obtained.

HPLC measurements following cleavage of the protecting groups show that the methyl isomers are present in the ratio of alpha:beta=53:47.

EXAMPLE 7

(1S,2S,3R,5R)-7,7-(2,2-dimethyl-trimethylenedioxy)-3-tertbutyldimethylsilyloxy-2-[(1E) (3S)-3-hydroxy-oct-1-enyl]bicyclo[3.3.0]octane 10.0 g of the ketone obtained in example A 4 are reduced according to example 3a). 8.05 g of the nonpolar 15alpha-hydroxy compound with $[alpha]_D-3.5°$ (chloroform, c=1), besides 1.30 g of polar 15beta-hydroxy isomer, is obtained.

We claim:

1. A process for the production of a 15α-hydroxybicyclo[3.3.0]octane of formula I

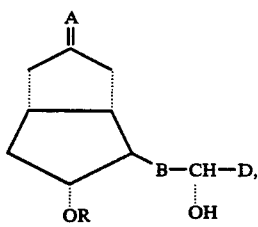
(I)

in which

A is —O—X—O—, =CH—(CH$_2$)$_3$—COOR', =CH—CH$_2$—O—CH$_2$—COOR' or =CH—(CH$_2$)$_3$—O—CH$_2$—CH$_2$—COOR'

X is straight-chain or branched alkylene of 1-7 C atoms

R' is C$_1$-C$_7$alkyl,

R is —SiR$_1$R$_2$R$_3$,

R$_1$, R$_2$ and R$_3$ can be the same or different and each is alkyl of 1-7 C atoms or phenyl, B is trans-CH=C(X') wherein the trans-configuration relates to the C chain, and X' is hydrogen or bromine, D is alkyl of 1-10 C atoms, alkenyl of 2-10 C atoms or alkynyl of 2-10 C atoms, comprising reducing, in the presence of a cerium (III) salt, a corresponding keto-bicyclo[3.3.0]octane of formula II

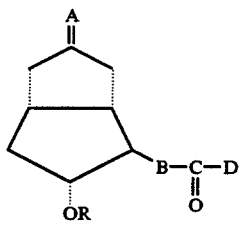
(II)

2. A process according to claim 1, wherein NaBH$_4$ is used as a reduction agent.

3. A process according to claim 1, wherein cerium (III) chloride is the cerium (III) salt.

4. A process of claim 1, further comprising converting the compound of formula I to iloprost.

5. A process of claim 1, further comprising converting the compound of formula I to cicaprost.

6. A process of claim 1, further comprising converting the compound of formula I to eptaloprost.

7. A process according to claim 2, wherein cerium (III) chloride is the cerium (III) salt.

8. A process of claim 1, wherein D contains a 16-alkyl group (carbacyclin nomenclature).

9. A process of claim 1, wherein D contains a 16-methyl group (carbacyclin nomenclature).

* * * * *